United States Patent [19]

Ockovic et al.

[11] Patent Number: 5,026,155
[45] Date of Patent: Jun. 25, 1991

[54] PROCESS FOR SIZING PARTICLES USING CONDENSATION NUCLEUS COUNTING

[75] Inventors: Richard C. Ockovic; Wayne T. McDermott; Alexander Schwarz, all of Allentown, Pa.

[73] Assignee: Air Products and Chemicals, Inc., Allentown, Pa.

[21] Appl. No.: 403,646

[22] Filed: Sep. 6, 1989

[51] Int. Cl.$^5$ .................. G01N 15/02; G01N 15/14
[52] U.S. Cl. .............................. 356/37; 356/336
[58] Field of Search .................. 356/37, 335, 356

[56] References Cited

U.S. PATENT DOCUMENTS

| | | | |
|---|---|---|---|
| 3,007,367 | 11/1961 | Rich | 356/37 |
| 3,632,210 | 1/1972 | Rich | 356/37 |
| 3,806,248 | 4/1974 | Sinclair | 356/37 |
| 4,128,335 | 12/1978 | Haberl et al. | 356/37 |
| 4,293,217 | 10/1981 | Bird, Jr. et al. | 356/37 |
| 4,790,650 | 12/1988 | Keady | 356/37 |

OTHER PUBLICATIONS

Stulzenburg, McMurry; "Counting Efficiency of an Ultrafine Aerosol Condensation Nucleus Counter: Theory and Experiment"; Aerosols: Formation & Reactivity, 1986, pp. 786–789.

Primary Examiner—Vincent P. McGraw
Attorney, Agent, or Firm—Geoffrey L. Chase; James C. Simmons; William F. Marsh

[57] ABSTRACT

A process for counting and sizing particles in gases in the size range of 0.0025 micrometers or greater using condensation nucleus counting wherein the condensing temperature of a saturated working fluid is incrementally adjusted to adjust sensitivity to differing sizes of particles and thus discriminate according to size.

15 Claims, 3 Drawing Sheets

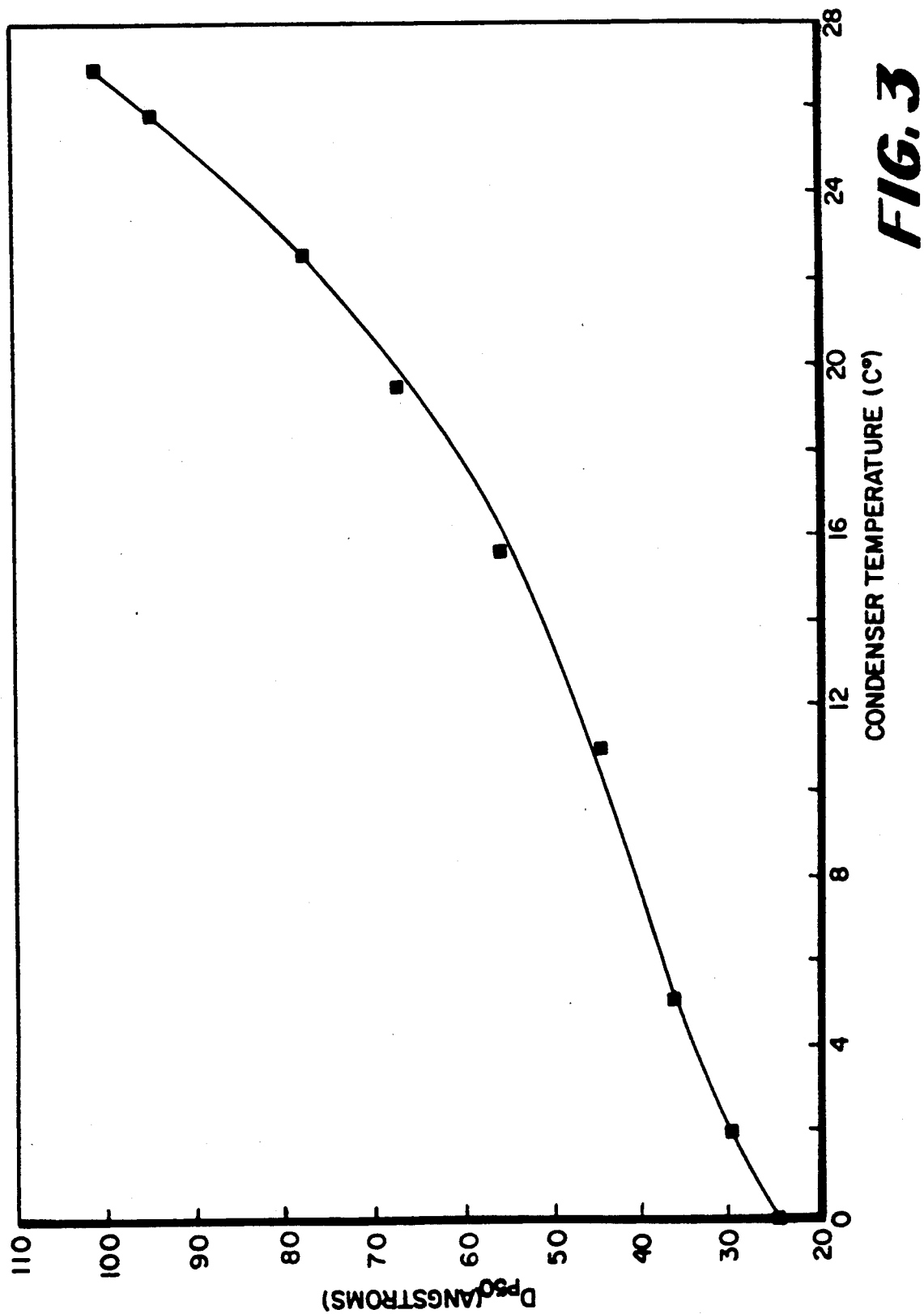

PROCESS FOR SIZING PARTICLES USING CONDENSATION NUCLEUS COUNTING

TECHNICAL FIELD

The present invention is directed to the discrimination of size in the counting of submicrometer particles in a gas stream. More specifically, the present invention is directed to using condensation nucleus counting wherein a saturated working fluid condenses on particles to form a droplet of increased size for subsequent counting, wherein the condensing temperature of the saturated working fluid is adjusted to change sensitivity to various particle sizes.

BACKGROUND OF THE PRIOR ART

The production of precision microelectronic devices, such as integrated circuits on silicon chips, requires extremely clean conditions. Significant reductions in device production yield have been traced to submicrometer particle deposition during the fabrication process. Fatal defects can be caused by particles which are a fraction of the minimum feature size of the device. The trend toward decreasing line widths in integrated circuits, etc. places increasing emphasis on the control of contaminant particles substantially smaller than 0.1 micrometer (1,000 angstroms) in the fabrication environment. Although many defects result from airborne contaminants in the clean room, it is also important to control particulate contamination within the process gas distribution system servicing the fabrication facility. High purity gases, such as nitrogen, flow through such systems directly to device processing equipment. Although these gases are typically filtered to high levels of cleanliness at the entrance to the distribution system, their cleanliness can only be assured through an accurate measurement of particulate concentrations within the supply system.

Previous experimental studies have demonstrated particulate concentrations of less than 0.3 per liter for all particles as small as 0.003 micrometer (30 angstroms) in clean room gas delivery systems. Such low particulate concentrations result in a correspondingly low arrival rate of detected particles when sampling with a particle counter. Low rates of particle detection tend to reduce the resolution of the particle detection test. That is, the difference between the particulate detection response and instrument background noise count rate becomes small. Therefore, long sample times (or large sample volumes) are required in order to statistically resolve the particulate count rate. This problem can be minimized by using a particle counter having a low background noise level. Various particle counters for determining the concentration of contaminant particles are known.

However, despite the abundance of prior art directed to counting quantitatively the amount of particle contamination in a gas, it is also important to not only determine the concentration of fine contaminant particles within the supply system, but to also determine their sizes so as to give a qualitative detection. Information regarding the size distribution of contaminant particles is as important in assessing their impact for the device fabrication process. Particle size determination should be performed to as small a particle as possible in order to meet the future as well as the present needs of the electronics industry. Therefore, a useful particle measuring device should determine the size distribution of fine, i.e., less than 0.1 micrometer, contaminant particles, with a low rate of spurious counts generated by instrument background noise.

Previous attempts to obtain continuous low noise sizing of fine contaminant particles have included laser particle spectrometers. These instruments determine the equivalent optical diameters of contaminant particles through a process of light scattering from individual particles. The intensity of scattered light is related directly to optical particle diameter through a separate calibration using particles of known diameter and refractive index. Such instruments typically classify particles into discrete size ranges (i.e., 0.1 to 0.2 micrometer, 0.2 to 0.3 micrometer, etc.). Continuous sizing of particles is not normally performed. Modern laser particle spectrometers typically function with low background noise for particles larger than 0.1 micrometer, but are noise limited in lower size detection capability because of light scattering from the subrange particles and gas molecules. Accurate particle sizing also depends upon the usually unknown refractive index and morphology of contaminant particles. In addition, the calibration of size versus scattered light intensity is subject to multi-valued response due to resonances in the scattering function for certain ranges of particle diameter. This reduces the confidence in overall particle size determination provided by the instrument.

Previous attempts to obtain low noise particle detection below 0.1 micrometer have included condensation nucleus counters. These instruments use continuous conductive cooling, continuous cooling through dilution or cooling through expansion to create a supersaturated aerosol mixture. Various substances have been used as a saturating medium, including water, alcohol, such as butanol, and perfluorinated organic compounds, such as perfluorodimethyldecalin. The fine particles act as nucleation sites for vapor condensation and subsequent droplet growth. Droplets grow to sufficient size to permit detection by conventional light scattering or light absorption techniques with negligible accompanying noise.

Such a condensation nucleus counter has been described in U.S. Pat. No. 4,790,650 wherein a device admits a gaseous flow into a saturator zone and then takes a portion of the flow through a chilled region to condense a working fluid on entrained particles to enlarge the diameter of the particle to facilitate counting by downstream means, such as an optical detection device. The text of this patent is incorporated by reference herein in its entirety.

Additional descriptions of condensation nucleus counters are found in the dissertation by M. R. Stolzenburg, particularly Chapter 5, titled "An Ultrafine Aerosol Condensation Nucleus Counter", and an article "A Condensation Nucleus Counter Design for Ultrafine Particle Detection Above 3 nm Diameter" by P. B. Keady, V. L. Denler. G. J. Sem, M. R. Stolzenburg and P. H. McMurray.

U.S. Pat. No. 4,293,217 discloses a continuous flow condensation nucleus counter and process for detecting small particle contaminants in gas streams.

U.S. Pat. No. 4,128,335 discloses a condensation nucleus counter with automatic ranging to determine particle sizing.

Additional patents include U.S. Pat. No. 3,806,248 and U.S. Pat. No. 3,632,210.

The theory for the operation of one type of condensation nucleus counter is set forth in an article by M. R. Stolzenburg and P. H. McMurray, entitled "Counting Efficiency of an Ultrafine Aerosol Condensation Nucleus Counter: Theory and Experiment".

Condensation nucleus counters are capable of detecting individual particles as small as 0.003 micrometer (30 angstroms) with negligible noise. However, the final droplet size is relatively uniform and independent of the original particle size. Therefore, information regarding the original contaminant particle size is lost in the condensation process. Therefore, the condensation nucleus counter when operated according to previous methods does not provide information on particle size distribution.

In order to use the condensation nucleus counter for measuring particle size distributions according to previous methods, upstream particle size selectors were required. These devices removed all particles from the contaminant gas stream, except those near a selected size or except those larger than the selected size. Examples of particle size selectors include electrostatic classifiers and diffusion batteries. The condensation nucleus counter in combination with the size selector can then be used to size contaminant particles and to measure their relative concentrations in the gas. However, the size selectors have been found to produce significant numbers of spurious particles through processes such as shedding and electrode sputtering. Therefore, these size selectors are of limited value in measuring the contamination levels of ultra clean systems requiring a low background noise.

Other techniques for measuring fine particle size distributions include particle capture on filters or impaction devices. Particle size distributions are then obtained using microscopy, gravimetric techniques or other methods. These techniques are tedious, expensive, sensitive to subjective interpretation and require batch sampling. In addition, the sampling times required to obtain measurable quantities of particulate matter from ultra clean gas systems is long when using these techniques.

Accordingly, there exists a need in the area of ultra clean gas handling and supply for a rapid, continuous, sensitive technique for measuring not only quantitative but qualitative parameters, specifically size, of submicrometer sized particles. The present invention as set forth below overcomes the disadvantages set forth above of the prior art and achieves the goal of rapid, continuous, sensitive determination of size in ultra clean gas systems.

BRIEF SUMMARY OF THE INVENTION

The present invention is a process for sizing particles in a particle-containing gas using condensation nucleus counting comprising, passing a particle-containing gas mixed with a working fluid vapor into a condensation zone, condensing working fluid on that portion of the particles of a minimum size corresponding to a minimum temperature of the condensation zone to form droplets, detecting the droplets and counting the number of droplets by appropriate sensing and tabulation, incrementally adjusting the degree of saturation of the working fluid in the gas by incrementally adjusting the temperature of the condensation zone to increase the degree of saturation at lower temperatures and performing the detection of droplets at each increment of temperature adjustment.

Preferably, the temperature of the condensation is incrementally adjusted downwardly to detect incrementally smaller particles.

Preferably, the particles are in the range of approximately 0.0025 micrometer up to 0.2 micrometer.

Preferably, the working fluid-containing gas is supersaturated in the condensation zone.

Preferably, the working fluid is a vapor at condensation zone conditions.

Preferably, the working fluid is selected from the group consisting of water, alcohols, such as butanol or propylene glycol, and perfluorinated organic compounds, such as perfluorodimethyldecalin.

Preferably, the temperature of the condensation zone is varied over the range of approximately $-3.6°$ C. up to 27° C.

Preferably, the particles are detected at an at least approximately 50% counting efficiency.

Preferably, the gas from which the particles are detected is selected from the group consisting of oxygen, nitrogen, hydrogen, helium, argon, krypton, nitrogen trifluoride, chlorine, fluorine, air and mixtures thereof.

Preferably, the droplets are detected by light scattering by the droplets. Alternatively, in the case of highly concentrated contamination the droplets are detected by light absorption by the droplets.

Preferably, the working fluid is saturated in a gas in a saturation zone before the working fluid-containing gas is introduced into the condensation zone. Optimally, the working fluid-containing gas is a portion of the particle-containing gas.

BRIEF DESCRIPTION OF THE DRAWINGS

FIG. 1b is an expanded partial view of FIG. 1a.

FIG. 3 is a graph of the smallest measurable particle diameters as a function of condenser temperature in a condensation nucleus counter.

DETAILED DESCRIPTION OF THE INVENTION

Figure 1A:
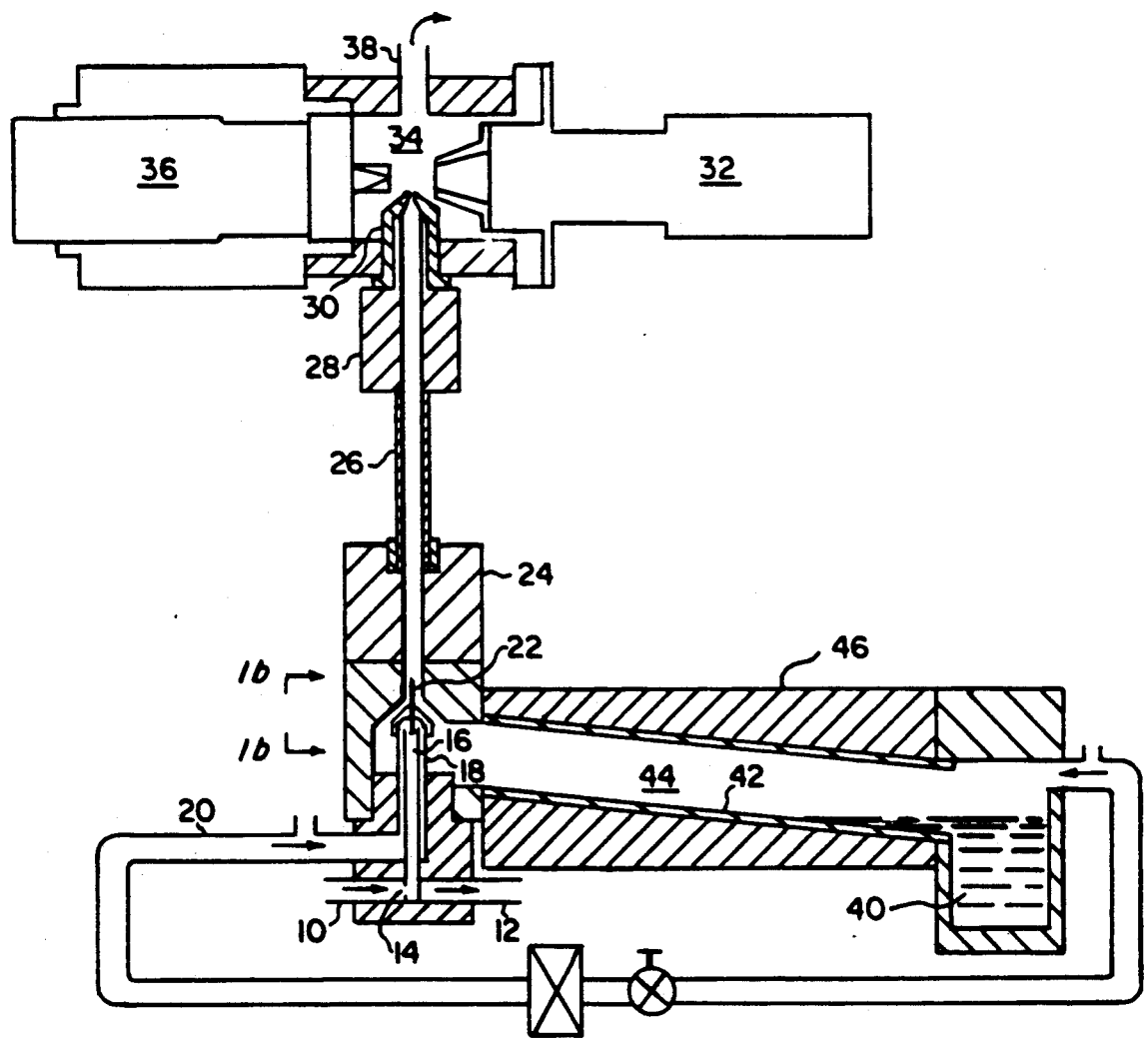
FIG. 1a is a schematic illustration of a condensation nucleus counter apparatus capable of operation in the manner of the process of the present invention.

Condensation nucleus counting is performed in an apparatus or counter which includes a saturation device, a gas inlet, a condenser and a detection zone for appropriate sensing and tabulation of droplets. A typical condensation nucleus counter is illustrated in FIG. 1a. With reference to that figure, the functioning of a condensation nucleus counter and the process of counting will be further described.

Figure 1B:
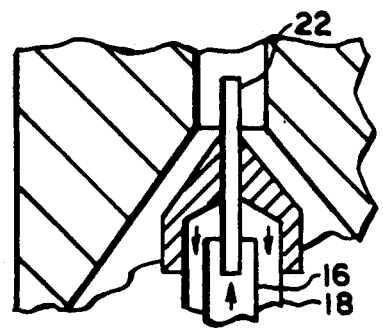

A particle-containing gas is introduced in line 10, into the counter. A portion of the gas enters orifice 14 and flows through a coaxial inner conduit 16. A radially centered and coaxial capillary tube 22, best viewed in FIG. 1b, extracts an inner core of the particle-containing gas, while the outer sheath flow of the particle-containing gas is detoured through an outer coaxial conduit 18. This outer sheath of gas is circuited in conduit 20 through a filter and appropriate valving to be introduced into the saturator 46, which is operated with a reservoir of working fluid 40. The gas in conduit 20 passes up through the saturation zone 44, wherein it comingles with vapors emanating from a wick or felt lining 42 in the saturator. The saturator is maintained at an elevated temperature sufficient to volatilize the working fluid into the gas. Such a temperature for instance could be 65° C. The resulting gas is a working fluid saturated and particle-free gas. The working fluid-containing gas from the saturation zone 44 and the particle-containing gas from capillary tube 22 comingle and mix in the insulation block 24, wherein the working fluid-containing gas encases the particle-containing gas in a coaxial sheath-like flow, passing through the condenser or condensation zone 26, 28, where the working fluid in the gas condenses on a portion of the particles in the particle-containing gas, which particles have a minimum size corresponding to a minimum temperature of the walls of the condenser apparatus. The particles act as nucleation sites for the droplets which form from condensing working fluid on the particles. The gas flow containing the droplets is focused through nozzle 30 and passes through a detection zone 34, wherein the droplets are sensed by light source 32, passing light across the flow of the droplet-containing gas and being detected by an optics photo detector 36, which provides for an appropriate electrical reading that can be transmitted to a tabulation means, such as a computer or data processing instrumentality. The resulting gas is removed in outlet 38.

The droplet sensing device typically consists of a light source, focusing optics, narrow slit, viewing volume, collecting optics and photodetector. Individual droplet detection is typically accomplished through a process of light scattering. A single pulse of scattered light is generated for each droplet travelling through the viewing volume. The photodetector converts the light pulses into electrical pulses which are typically counted in a triggering circuit. Tabulated droplet counts can be converted directly to particle concentration in the gas stream using the known gas flow rates.

The present invention is the recognition that by varying the temperature of the condensation zone 28, the condensation nucleus counting process can be varied with regard to its sensitivity to various sizes of contaminant particles. More specifically, by incrementally reducing the temperature of the condensation zone, the condensation nucleus counting process can be made more sensitive to increasingly smaller sized particles. By operating over a continuously incrementally decreasing temperature range for the condensation zone, particles of incrementally decreasing size can be measured and the relative count of such particles will provide a relative sizing of the overall particle distribution. By also calibrating the condensation nucleus counter against a known particle size generator or splitting a stream of the sensed particles and counting with an alternative size determination device, the condensation nucleus counter can be calibrated so that not only the relative size, but the absolute size of particles in each incremental counting at the various temperatures will be provided.

The process of nucleation and droplet growth in a condensation nucleus counter is strongly affected by the degree of supersaturation of the working fluid in its gas. For a continuous flow, thermal conduction condensation nucleus counter, heat removal and super saturation are achieved in the condenser tube or condensation zone. The higher the supersaturation, the smaller the particle that can be used as a nucleation site. Therefore, a lower gas temperature in the condenser decreases the minimum diameter $D_p$ of particles capable of acting as droplet nucleation sites. This results in a decrease in the minimum detectable particle size. All particles larger than the minimum detectable particle size can act as nucleation sites and be detected as droplets. Therefore, information regarding the particle size density distribution of a steady gas containing particles can be obtained by varying the condenser or condensation zone temperature (and the corresponding minimum detectable particle size) while measuring the concentration of particles. Since the condensation nucleus counter has a low background noise, particle size distributions can be measured using this process even for contamination present in ultra clean gas systems.

The process can be demonstrated by introducing particles of a known narrow size range into the condensation nucleus counter and measuring the efficiency with which the instrument counts the particles. The measurement is repeated over a range of particle sizes to obtain the characteristic response curve of the instrument, known as the counting efficiency curve. The counting efficiency is approximately one for large particles, that is, those having diameters well above the minimum detectable particle size. However, the counting efficiency falls to zero at the minimum detectable particle size. The diameter corresponding to the minimum detectable size varies with condenser temperature according to the present invention. Therefore, the overall counting efficiency curve varies with condenser temperature.

Figure 2:
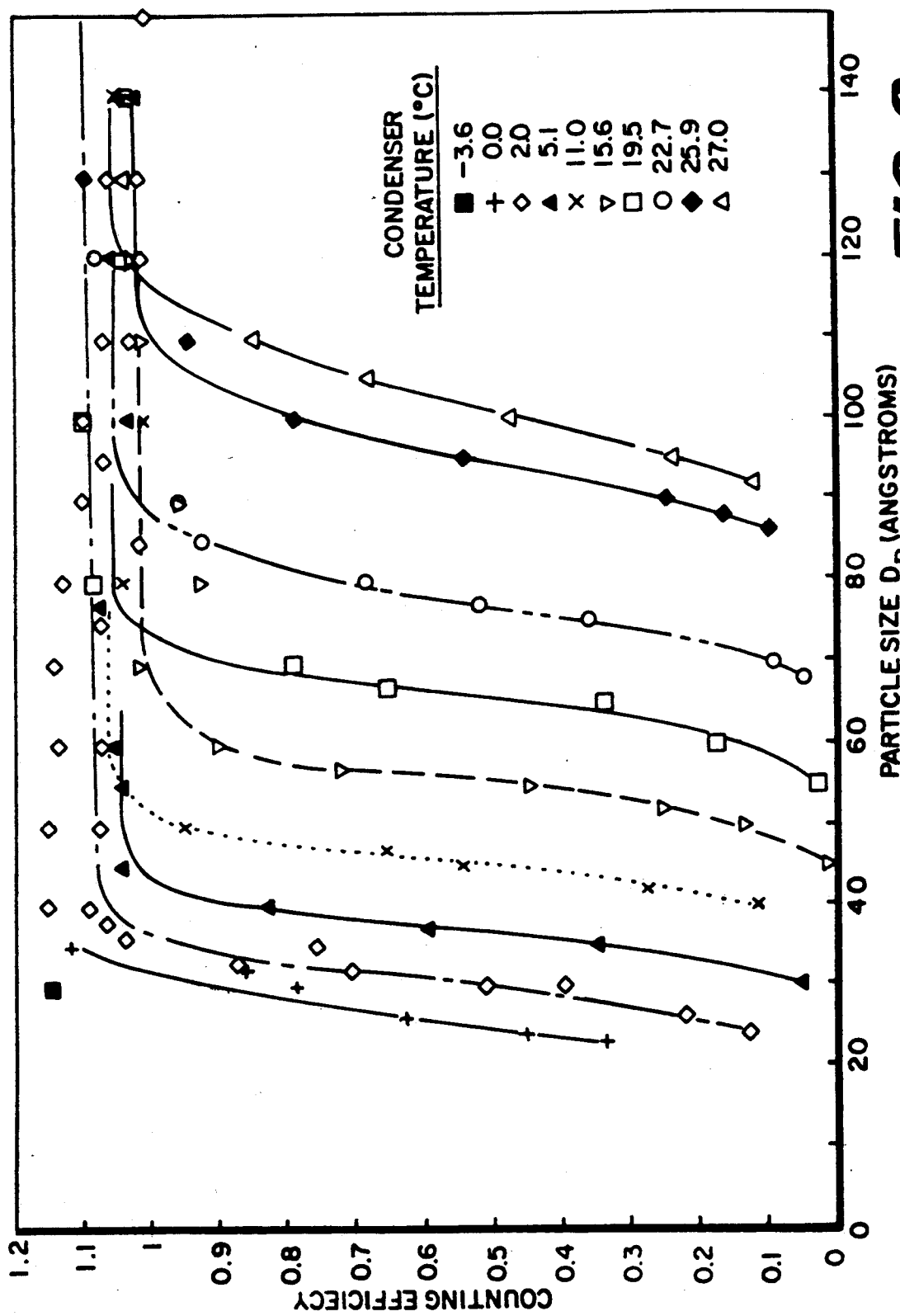
FIG. 2 is a graph of counting efficiency as a function of particle size at varying condenser temperatures of a condensation nucleus counter.

For the tests represented in FIG. 2 and FIG. 3 described herein, particles were produced by vaporizing sodium chloride in heated nitrogen at approximately 900° C. and then quickly diluting the mixture with cool filtered nitrogen. The rapid dilution produced fine sodium chloride particles having a continuous distribution of sizes ranging from 0.0025 micrometer to 0.2 micrometer. The resulting aerosol was reduced to a narrow size range by flowing it through an electrostatic classifier, or differential mobility analyzer. The differential mobility analyzer rejects all particles except those near a selected size. The aerosol is first charge neutralized by exposing it to the radiation from a Krypton −85 source. Nearly all of the neutralized particles contain either a zero or a unit charge. The neutralized aerosol is then flowed into a differential mobility analyzer. The mobility analyzer is used to extract particles having a selected electrical mobility. The electrical mobility $Z_p$(cm$^2$/volt-sec) of a singly charged particle is related to the particle size as follows:

$$Z_p = \frac{e \, C \times 10^7}{3\pi \mu D_p}$$

where $e = 1.6 \times 10^{-19}$ coulombs, C is the dimensionless slip correction factor for the particle and $\mu$ (poise) is the gas viscosity. The differential mobility analyzer flows the aerosol and a filtered sheath gas through two concentric circular electrodes having radii $r_1$ and $r_2$ and length L (cm). A dc voltage V is applied to the electrodes to generate an electric field perpendicular to the flow direction. The trajectories of the charged particles are altered by the electric field. The paths followed by the diverted particles are determined by their specific electrical mobilities. Particles following a selected path are removed through a slit at the end of the electrodes. All other particles are vented or deposited on the electrodes. The electrical mobility of the extracted particles is given by:

$$Z_p = \frac{[q_t - \tfrac{1}{2}(q_s + q_a)]\ln(r_2/r_1)}{2\pi VL}$$

where $q_t$ is the total flow rate through the analyzer, $q_s$ is the slit flow rate and $q_a$ is the inlet aerosol flow rate (cm$^3$/sec). The resulting narrow band sodium chloride aerosol was then split into two streams. One stream flowed to the condensation nucleus counter, while the other stream was directed into an aerosol electrometer. Measurements of particle concentration obtained from the condensation nucleus counter were then directly compared to those obtained from the electrometer in order to determine counting efficiency of the condensation nucleus counter. The particle size of the narrow band aerosol was then varied by adjusting the voltage of the differential mobility analyzer in order to obtain the counting efficiency curve of the condensation nucleus counter.

The condensation nucleus counter's counting efficiency varies strongly with particle size at each condenser temperature, as can be seen in FIG. 2. In this graph, the condenser temperature is defined as the measured temperature of the condenser tube wall of the condensation zone and not the gas temperatures themselves. This graph shows that the counting efficiency curves of a condensation nucleus counter were relatively steep over a range of condenser temperatures. This indicates a relatively sharp lower size cutoff. Therefore, when used with this process, the condensation nucleus counter can be used to detect and size classify particles subject to condensation of a working fluid from a gas. This sizing operation can be performed with a relatively high degree of cutoff resolution. The relationship between minimum detectable particle size and condenser temperature for a condensation nucleus counter is shown in FIG. 3. The quantity $D_{p50}$ refers to the particle size which the condensation nucleus counter is capable of detecting and counting at a rate of 50% of the particles. The data points shown in FIG. 3 were obtained from the efficiency curves shown in FIG. 2.

FIG. 3 can be used as a calibration curve to set the lower cutoff size for a condensation nucleus counter. With the condenser wall temperature set to a desired value, the condensation nucleus counter can be used to directly measure the total concentration of all contaminant particles larger in size than the corresponding $D_{p50}$. The condenser wall temperature is easily adjusted using manual or automatic external control of the condenser's thermoelectric cooler power supply. The present invention provides the desired low noise measurement required to obtain particle size distribution within an ultra clean gas system.

The saturation ratio "s" of vapor in equilibrium with a droplet of diameter $D_p$ is given by the Kelvin equation:

$$s = \exp[4\sigma M/(D_p R T \rho_d)]$$

where "s" is defined as:

$$s = p/p_s(T)$$

The value "p" is the vapor pressure of the working fluid. The value $p_s(T)$ is the saturation vapor pressure at the local temperature T(°K.) and can be calculated from available thermodynamic data using the Clausius-Clapeyron equation. The term "sigma" $\sigma$ (dynes/cm) is the droplet surface tension. The term "M" (gm/mole) is the molecular weight of the condensing vapor. The term "rho" $\rho_d$(gm/cm$^3$) is the droplet density. The term "R" equals 1.987 cal(mole °K). A value of "s" greater than 1 indicates a condition of supersaturation. A lower gas temperature in the condenser results in an increased saturation ratio "s", thereby decreasing the minimum diameter $D_p$ of particles capable of acting as nucleation sites. This results in a decrease in the minimum detectable particle size. All particles larger than the Kelvin diameter can act as nucleation sites for subsequent droplet growth and detection by the condensation nucleus counting process.

The saturation ratio "s" of the mixture varies with position in the steadily flowing condensation nucleus counter condenser tube or condensation zone. The saturation ratio is determined by simultaneous processes of heat transfer and vapor diffusion within the condensation zone. Therefore, the distribution of saturation ratio within the condenser incrementally changes as the condenser wall temperature is incrementally changed. This distribution can be obtained analytically through a solution of the appropriate heat and mass transfer equations for laminar flow through a tube. The general result of this solution is that the level of supersaturation throughout the condensation zone incrementally increases as the condenser tube wall temperature is incrementally decreased. This variation in saturation ratio with condenser temperature causes the observed change in minimum detectable particle size.

The present invention differs from previous attempts to solve the problem of particle size determination, in that no upstream size selector is required to obtain particle size information from a condensation nucleus counting process. A single, stand-alone condensation nucleus counter having a continuously adjustable condenser wall temperature provides particle size selectivity. Therefore, less overall instrumentation is required and background noise level is reduced. The process of the present invention permits a direct measurement of the cumulative size distribution of contaminant particles in a gas. That is, the condensation nucleus counting process directly provides a reading of all particles larger in size than the selected cutoff value. This method of data representation is most useful to microelectronics manufacturers who require information on total concentrations of particles larger than some critical size limit. The present invention utilizes all of the advantages of condensation nucleus counting technology to provide particle detection below 0.1 micrometer while incorporating the advantage of particle sizing provided alternatively by laser spectrometry.

In addition to applicability of the process of the present invention to a particle counter as illustrated in FIG 1a, the process is also amenable to other particle counters such as those wherein the particle-containing gas itself directly picks up working fluid vapor without the requirement for a separate sidestream to collect the working fluid. Other departures from preferred embodiments can be contemplated without departing from the scope of the claims of this invention.

The present invention has been set forth with regard to particular preferred embodiment, however, the scope of the present invention should be ascertained from the claims which follow.

We claim:

1. A continuous process for sizing particles in a particle-containing gas using condensation nucleus counting, comprising:
   (a) passing a particle-containing gas mixed with a working fluid vapor into a condensation zone,
   (b) condensing working fluid on that portion of the particles of a minimum size corresponding to a minimum temperature of the condensation zone to form droplets,
   (c) detecting the resulting droplets and counting the number of droplets by appropriate sensing of scattered light for each droplet and tabulation,
   (d) incrementally adjusting the degree of saturation of the working fluid in the gas by incrementally adjusting the temperature of the condensation zone to increase the degree of saturation at lower temperatures, and
   (e) performing step c) at each increment of temperature adjustment.

2. The process of claim 1 wherein the temperature of the condensation zone is incrementally adjusted downwardly to detect incrementally smaller particles.

3. The process of claim 1 wherein the particles are in the range of approximately 0.0025 micrometer to 0.2 micrometer.

4. The process of claim 1 wherein the working fluid-containing gas is supersaturated.

5. The process of claim 1 wherein the working fluid is a vapor at condensation zone conditions.

6. The process of claim 1 wherein the working fluid is selected from the group consisting of water, alcohols and perfluorinated organic compounds.

7. The process of claim 1 wherein the working fluid is butanol.

8. The process of claim 1 wherein the working fluid is perfluorodimethyldecalin.

9. The process of claim 1 wherein the temperature of the condensation zone is varied over the range of approximately $-3.6°$ C. to $27°$ C.

10. The process of claim 1 wherein the particles are detected at an at least approximately 50% counting efficiency.

11. The process of claim 1 wherein the gas is selected from the group consisting of oxygen, nitrogen, hydrogen, helium, argon, krypton, nitrogen trifluoride, chlorine, fluorine, air and mixtures thereof.

12. The process of claim 1 wherein the droplets are detected by light scattering by the droplets.

13. The process of claim 1 wherein the temperature of the saturation zone is held at approximately $65°$ C.

14. The process of claim 1 wherein the working fluid is saturated in a gas in a saturation zone before the working fluid-containing gas is introduced into the condensation zone.

15. The process of claim 14 wherein the working fluid-containing gas is derived from a portion of the particle-containing gas.

* * * * *